(12) United States Patent
Ishihara

(10) Patent No.: US 7,959,572 B2
(45) Date of Patent: Jun. 14, 2011

(54) ULTRASONIC DIAGNOSTIC APPARATUS, IMT MEASUREMENT METHOD, AND IMT MEASUREMENT PROGRAM

(75) Inventor: Keitarou Ishihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 680 days.

(21) Appl. No.: 11/968,865

(22) Filed: Jan. 3, 2008

(65) Prior Publication Data

US 2008/0171939 A1    Jul. 17, 2008

(30) Foreign Application Priority Data

Jan. 15, 2007  (JP) ................................. 2007-005339

(51) Int. Cl.
A61B 8/00  (2006.01)
(52) U.S. Cl. .......................... 600/437; 600/407; 382/128
(58) Field of Classification Search .................. 600/407, 600/437; 382/128
See application file for complete search history.

(56) References Cited

U.S. PATENT DOCUMENTS

| | | | | |
|---|---|---|---|---|
| 7,686,764 | B2 * | 3/2010 | Watanabe et al. | ............. 600/443 |
| 2005/0096528 | A1 * | 5/2005 | Fritz et al. | ..................... 600/407 |
| 2009/0024032 | A1 * | 1/2009 | Kato et al. | ..................... 600/443 |

FOREIGN PATENT DOCUMENTS

| | | |
|---|---|---|
| JP | 11-318896 A | 11/1999 |
| JP | 2004-357892 A | 12/2004 |
| WO | 2005/032375 A2 | 4/2005 |

OTHER PUBLICATIONS

Hiroyuki Toide, Proper Ultrasonic Examination of Blood Vessels, Ultrasonic examination technique, 2006, p. 80, vol. 31, No. 2 (Partial translation of p. 80, right col., lines 3-8).
Extended European Search Report corresponding to European Patent Application No. 08000496.3, dated Jul. 16, 2010.
Arnold P.G. Hoeks, et al., Automated Detection of Local Artery Wall Thickness Based on M-Line Signal Processing, XP-002589193, Ultrasound in Med. & Biol., vol. 23, No. 7 pp. 1017-1023, 1997.

* cited by examiner

Primary Examiner — Tse Chen
Assistant Examiner — Joel F Brutus
(74) Attorney, Agent, or Firm — Sughrue Mion, PLLC

(57) ABSTRACT

An ultrasonic diagnostic apparatus by which highly quantitative IMT (intima media thickness) measurement with little variations depending on examiners can be performed. The ultrasonic diagnostic apparatus includes: an ultrasonic probe for transmitting ultrasonic waves to an object to be inspected and receiving ultrasonic echoes generated by reflection of the ultrasonic waves in the object to output reception signals; a signal processing unit for performing at least envelope detection processing on the reception signals outputted from the ultrasonic probe to generate envelope data; a boundary detecting unit for detecting two boundaries representing intima media of a blood vessel based on difference or differential of values of the envelope data and amounts of change in the values of the envelope data; and an IMT calculating unit for calculating an IMT of the blood vessel based on the two boundaries detected by the boundary detecting unit.

20 Claims, 9 Drawing Sheets

ULTRASONIC DIAGNOSTIC APPARATUS, IMT MEASUREMENT METHOD, AND IMT MEASUREMENT PROGRAM

BACKGROUND OF THE INVENTION

1. Field of the Invention

The present invention relates to an ultrasonic diagnostic apparatus having a function of measuring intima media thickness (IMT) of a blood vessel based on reception signals obtained by transmitting ultrasonic waves to an object to be inspected and receiving ultrasonic waves from the object. Further, the present invention relates to an IMT measurement method and an IMF measurement program to be used when such IMT measurement is performed.

2. Description of a Related Art

Recent years, intima media thickness has attracted attention as an indicator for determination of arteriosclerosis. Referring to FIG. 9, an arterial wall has a three-layer structure including an intima 901, a media 902, and an adventitia 903. IMT refers to a thickness of the intima 901 and the media 902 of them, i.e., a length from a boundary between a vascular lumen 900 and the intima 901 to a boundary between the media 902 and the adventitia 903. From recent research, it has been found that the intima media thickness increases and a plaque is formed as arteriosclerosis progresses. Here, the plaque is a part where a vessel wall is raised inwardly. Tissues of the plaque may be various tissues such as blood clot or fatty or fibrous tissues, and cause carotid artery stenosis, cerebral infarction, cerebral ischemia, and so on.

FIGS. 10 and 11 are schematic diagrams showing part of a carotid artery. As shown in FIGS. 10 and 11, the blood pumped from the heart is introduced into a common carotid artery (CCA) 911, and divided into an external carotid artery (ECA) 912 that connects to an artery of the face and an internal carotid artery (ICA) 913 that connects to an artery of the brain.

The above-explained IMT is measured by ultrasonic examination (carotid artery ultrasonic examination). That is, an ultrasonic probe including an ultrasonic transducer array, in which plural ultrasonic transducers are arranged, is brought into contact with the cervical part of an object to be inspected (a patient) to transmit ultrasonic waves. Here, the reason the IMT is measured in the carotid artery is that the carotid artery is a favorite site of arteriosclerosis. In this regard, the plural ultrasonic transducers are sequentially driven and an ultrasonic beam is formed by synchronization of plural ultrasonic waves, and thereby, the object is electronically scanned. Thus transmitted ultrasonic waves are reflected on the surface of a structure within the object (a boundary between different tissues), and resulting ultrasonic echoes are received by the ultrasonic probe and reception signals are generated. Those reception signals are processed in an ultrasonic diagnostic apparatus main body connected to the ultrasonic probe, and thereby, an ultrasonic image is generated. Further, an examiner (an operator such as a doctor) measures the vessel wall by using a vernier caliper or the like in the ultrasonic image generated as described above, and therefore, the IMT is obtained. Furthermore, the level of arteriosclerosis is measured based on the IMT, and the vessel status throughout the body including the heart and the brain is estimated based on the result.

However, according to the measurement method, there are problems that the measurement requires long time and the measurement accuracy largely varies depending on the levels of skill of examiners. In order to actively utilize IMT in mass checkup or the like, efficient IMT measurement requiring short time and providing measurement results that vary little depending on examiners is desired.

As a related technology, Hiroyuki TOIDE, "PROPER ULTRASONIC EXAMINATION OF BLOOD VESSELS", Ultrasonic examination technique, Vol. 31, No. 2 (2006), pp. 80 discloses precautions and points for ultrasonic examination of blood vessels. For example, in carotid artery ultrasonic examination, the vessel diameter, maxIMT and meanIMT are measured. Here, a plaque 915 is likely formed in a region where the direction of blood flow changes like in the vicinity of the entrance of common carotid artery or the vicinity of vascular bifurcation (BIF) 914. Accordingly, as shown in FIG. 10, the maxIMT is measured at two positions of the common carotid artery 911 and a region (BIF to ICA) from the bulbous part (vascular bifurcation (BIF) 914) to the internal carotid artery 913. Further, as shown in FIG. 11, meanIMT is obtained by measuring maxIMT and two IMTs at positions "a" and "c" on both sides at 1 cm from it, and calculating an average value of the three points as follows: $\{\text{maxIMT}+\text{IMT}(a)+\text{IMT}(c)\}/3$.

Japanese Patent Application Publication JP-A-11-318896 discloses an intima media thickness measurement apparatus including an ultrasonic unit that outputs data of images imaged by using ultrasonic waves as digital data, a data transmission unit that transmits the digital output of the ultrasonic unit by using optical coupling, and a data analysis unit that calculates the intima media thickness of a blood vessel based on the image data of the blood vessel transmitted by the data transmission unit, and the data analysis unit calculates a reference position based on a moving average value of intensity values of the digital image data and calculates the intima media thickness of the blood vessel based on the local maximum value and the local minimum value of the intensity values within a predetermined pixel range from the reference position toward the vessel wall of the blood vessel.

In JP-A-11-318896, the IMT value is automatically calculated by searching for peak values of intensity. Here, the intensity representing the intima side boundary (the boundary between the vascular lumen and the intima) is not so high and it may be difficult to detect the boundary, and accordingly, regression curve correction is performed in JP-A-11-318896. Alternatively, an average value of detected points may be used. However, according to the method, when there are many points that cannot be detected, the accuracy in IMT measurement is reduced and the true value is impossible to be obtained when maxIMT is calculated.

Alternatively, simply searching for the boundary based on the peak values of intensity may cause detection errors when the noise is great. For example, as shown in FIG. 12, in the case where plural relatively large peaks (1)-(3) are observed in intensity data, although the maximum peak (3) is actually the adventitia side boundary (the boundary between the media and the adventitia) of IMT and the adjacent peak (2) is the intima side boundary, the first peak (1) is detected as the intima side boundary and the next peak (2) is detected as the adventitia side boundary when the boundary search is started from the base position. Thus, diagnoses utilizing maxIMT will be largely affected.

Japanese Patent Application Publication JP-P2004-357892A discloses an ultrasonic diagnostic apparatus that displays an image within a body of an examinee based on reflected ultrasonic waves acquired from within the body by using an ultrasonic probe and performs measurement of intima media thickness of a blood vessel. The ultrasonic diagnostic apparatus includes (a) measurement region setting means for setting a region as an object to be measured within the displayed image, (b) vessel wall detecting means for detecting vessel wall existing in one or plural positions within the measurement region, and (c) IMT measurement means for performing measurement of intima media thickness with respect to each of the detected vessel walls. The vessel wall detecting means detects positions where intensity values of pixels suddenly change, and then, determines the position of the vessel wall based on the distance between adjacent intensity value sudden change positions. The IMT measurement means determines the intima media thickness with respect to each vessel wall based on the distance between adjacent intensity value sudden change positions that belong to the same vessel wall.

Here, in a measurement line that passes through one vessel wall, intensity value sudden change positions are observed at two positions of the vascular lumen side boundary and the adventitia side boundary of the intima media thickness. Accordingly, in JP-P2004-357892A, in the case where three or more intensity value sudden change positions are detected in a certain measurement line, whether or not those intensity value sudden change positions belong to the same vessel wall is determined based on the distances between the positions (paragraph 0016). However, since a vessel wall has continuity in the azimuth direction, it is not rational that the vessel wall status is determined based on the intensity change in the distance (depth) direction.

SUMMARY OF THE INVENTION

The present invention has been achieved in view of the above-mentioned problems. A purpose of the present invention is to provide an ultrasonic diagnostic apparatus by which highly quantitative IMT measurement with little variations depending on examiners can be performed. Further, another purpose of the present invention is to provide an IMT measurement method and an IMT measurement program to be used for the IMT measurement in the ultrasonic diagnostic apparatus.

In order to accomplish the above-mentioned purposes, an ultrasonic diagnostic apparatus according to one aspect of the present invention includes: an ultrasonic probe for transmitting ultrasonic waves to an object to be inspected and receiving ultrasonic echoes generated by reflection of the ultrasonic waves in the object to output reception signals; signal processing means for performing at least envelope detection processing on the reception signals outputted from the ultrasonic probe to generate envelope data; boundary detecting means for detecting two boundaries representing intima media of a blood vessel based on difference or differential of values of the envelope data and amounts of change in the values of the envelope data; and IMT (intima media thickness) calculating means for calculating an IMT of the blood vessel based on the two boundaries detected by the boundary detecting means.

Further, an IMT (intima media thickness) measurement method according to one aspect of the present invention is a method of measuring an IMT of a blood vessel based on envelope data in an ultrasonic diagnostic apparatus for transmitting ultrasonic waves to an object to be inspected and receiving ultrasonic echoes generated by reflection of the ultrasonic waves in the object to obtain reception signals, and performing at least envelope detection processing on the reception signals to generate the envelope data, and the method includes the steps of: (a) detecting two boundaries representing intima media of the blood vessel based on difference or differential of values of the envelope data and amounts of change in the values of the envelope data; and (b) calculating the IMT of the blood vessel based on the two boundaries detected at step (a).

Furthermore, an IMT (intima media thickness) measurement program according to one aspect of the present invention is a program embodied on a computer readable medium, for measuring an IMT of a blood vessel based on envelope data in an ultrasonic diagnostic apparatus for transmitting ultrasonic waves to an object to be inspected and receiving ultrasonic echoes generated by reflection of the ultrasonic waves in the object to obtain reception signals, and performing at least envelope detection processing on the reception signals to generate the envelope data, and the program activates a CPU to execute the procedures of: (a) detecting two boundaries representing intima media of the blood vessel based on difference or differential of values of the envelope data and amounts of change in the values of the envelope data; and (b) calculating the IMT of the blood vessel based on the two boundaries detected at procedure (a).

According to the present invention, the boundaries are detected by focusing attention on change (difference or differential) and amounts of change in intensity of pixels forming an ultrasonic image, and therefore, highly quantitative IMT measurement with little variations depending on examiners can be performed.

DESCRIPTION OF THE PREFERRED EMBODIMENTS

Hereinafter, a preferred embodiment of the present invention will be explained in detail with reference to the drawings. The same reference numbers are assigned to the same component elements and the description thereof will be omitted.

Figure 1:
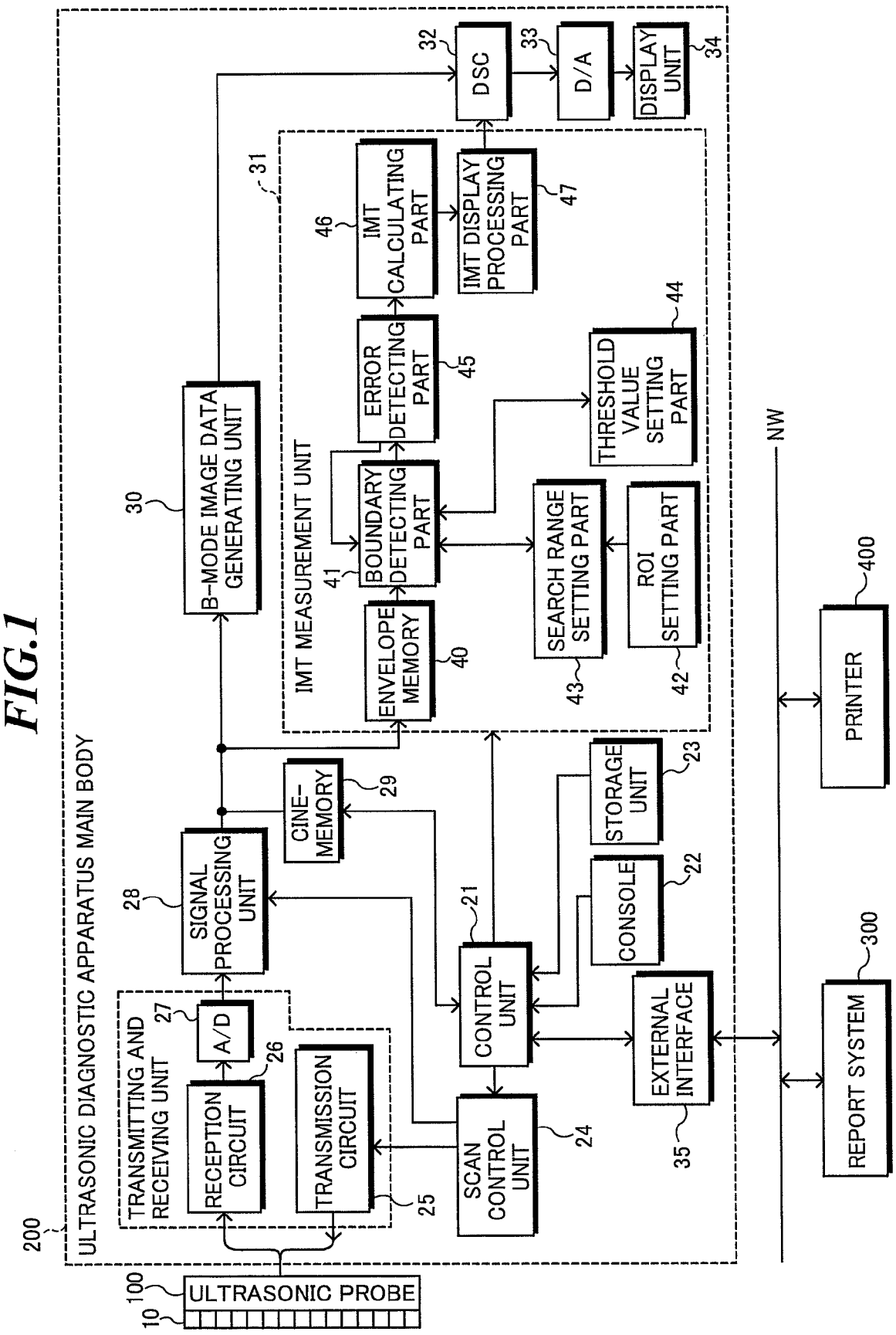
FIG. 1 is a block diagram showing a configuration of an ultrasonic diagnostic apparatus according to one embodiment of the present invention.

FIG. 1 is a block diagram showing an ultrasonic diagnostic apparatus according to one embodiment of the present invention. The ultrasonic diagnostic apparatus includes an ultrasonic probe 100 for transmitting and receiving ultrasonic waves, and an ultrasonic diagnostic apparatus main body 200 for controlling transmission and reception of ultrasonic waves and generating an ultrasonic image based on acquired reception signals. The ultrasonic diagnostic apparatus main body 200 has a function of measuring intima media thickness (IMT) of an artery. Both of them are connected to each other by a cable. Further, such an ultrasonic diagnostic apparatus may be connected to a report system 300 or printer 400 via a network NW such as a LAN (local area network) or the like.

The ultrasonic probe 100 is a probe of convex type, linear scan type, or sector scan type to be used in contact with an object to be inspected. The ultrasonic probe 100 includes plural ultrasonic transducers 10 that form one-dimensional or two-dimensional transducer array. These ultrasonic transducers 10 transmit an ultrasonic beam to the object according to applied drive signals, and receive ultrasonic echoes reflected from the object to output reception signals.

Each ultrasonic transducer is constituted from a vibrator in which electrodes are formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulsed or continuous wave voltage is applied to the electrodes of the vibrator, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves to generate electric signals. These electric signals are outputted as reception signals of the ultrasonic waves.

Alternatively, as the ultrasonic transducers, plural kinds of elements of different ultrasonic conversion types may be used. For example, the above-mentioned vibrators are used as elements for transmitting ultrasonic waves and photo-detection type ultrasonic transducers are used as elements for receiving ultrasonic waves. The photo-detection type ultrasonic transducer is for detecting ultrasonic signals by converting the ultrasonic signals into optical signals, and constituted from a Fabry-Perot resonator or fiber Bragg grating, for example.

The ultrasonic diagnostic apparatus main body 200 includes a control unit 21 that controls operation of the entire ultrasonic diagnostic apparatus, a console 22, a storage unit 23, a scan control unit 24, a transmitting and receiving unit including a transmission circuit 25, a reception circuit 26, and an A/D converter 27, a signal processing unit 28, a cine-memory 29, a B-mode image data generating unit 30, an IMT measurement unit 31, a DSC (digital scan converter) 32, a D/A converter 33, a display unit 34, and an external interface 35.

The console 22 is an input device to be used by an examiner (operator) when various commands and information are inputted to the ultrasonic diagnostic apparatus main body 200. The console 22 includes character input keys (a keyboard) to be used when patient information and so on are inputted, a track ball to be used when a region is designated on a screen, and various input buttons. Further, the console 22 includes a freeze button for switching between the live mode (moving image) and freeze mode (still image) with respect to the ultrasonic image being displayed on the screen, and a freeze signal and a freeze release signal are alternately inputted at each time when the freeze button is pushed down.

The storage unit 23 is constituted from a hard disk, memory, or the like, and stores programs (software) to be used for activating a CPU included in the ultrasonic diagnostic apparatus main body 200 to execute various kinds of processing, information to be used for the processing, and so on.

The scan control unit 24 sequentially sets transmission directions of ultrasonic beams or reception directions of ultrasonic echoes under the control of the control unit 21, and has a transmission control function of selecting transmission delay patterns according to the set transmission directions and a reception control function of selecting reception delay patterns according to the set reception directions.

Here, the transmission delay pattern refers to a delay time pattern to be provided to the drive signals for forming an ultrasonic beam in a desired direction by using the ultrasonic waves transmitted from the plural ultrasonic transducers 10, and the reception delay pattern refers to a delay time pattern to be provided to the reception signals for extracting ultrasonic echoes from a desired direction by using the ultrasonic waves received by the plural ultrasonic transducers. Plural transmission delay patterns and plural reception delay patterns are stored in a memory or the like.

The transmission circuit 25 generates plural drive signals to be respectively applied to the plural ultrasonic transducers 10. At that time, the transmission circuit 25 provides respective delay times to the plural drive signals based on the transmission delay pattern selected by the scan control unit 24. Here, the transmission circuit 25 may adjust the amounts of delay of the plural drive signals and supply the signals to the ultrasonic probe 100 such that the ultrasonic waves to be transmitted from the plural ultrasonic transducers 10 form an ultrasonic beam, or may supply plural drive signals to the ultrasonic probe 100 such that the ultrasonic waves to be transmitted at once from the plural ultrasonic transducers 10 reach the entire imaging region of the object.

The reception circuit 26 amplifies the reception signals respectively outputted from the plural ultrasonic transducers 10, and the A/D converter 27 converts the analog reception signals amplified by the reception circuit 26 into digital reception signals (also referred to as "RF data" in this application). The RF data outputted from the A/D converter 27 is inputted to the signal processing unit 28. The signal processing unit 28 performs reception focus processing by providing the respective delay times to the plural reception signals represented by the RF data based on the reception delay pattern selected by the scan control unit 24, and adding those reception signals to one another. Through the reception focus processing, sound ray data, in which the focal point of the ultrasonic echoes is narrowed, is formed.

Furthermore, the signal processing unit 28 corrects the sound ray data for attenuation due to distance according to the depths of the reflection positions of ultrasonic waves through STC (sensitivity time gain control), and then, performs envelope detection processing with a low-pass filter or the like thereon to generate envelope data. The value of the envelope data corresponds to intensity of reflection of ultrasonic waves in the object, and also corresponds to an intensity value of a pixel on a sound ray in an ultrasonic image. As below, the envelope data is also referred to as intensity data.

A series of envelope data (intensity data) generated by the signal processing unit 28 are sequentially stored in the cine-memory 29 and supplied to the B-mode image data generating unit 30. The cine-memory 29 has a memory capacity for storing the envelope data for at least one frame, more preferably for plural frames. The B-mode image data generating unit 30 performs pre-process processing such as Log (logarithmic) compression and gain adjustment on the envelope data to generate B-mode image data, and outputs the generated B-mode image data to the DSC 32.

The IMT measurement unit 31 has an envelope memory 40, a boundary detecting part 41, an ROI setting part 42, a search range setting part 43, a threshold value setting part 44, an error detecting part 45, an IMT calculating part 46, and an IMT display processing part 47, and measures IMT based on the envelope data (intensity data).

In the embodiment, the IMT measurement unit 31 (the respective parts except for the envelope memory 40) is constituted from a central processing unit (CPU) and software (an IMT measurement program) for activating the CPU to perform various kinds of processing. However, they may be constituted from digital circuits or analog circuits. Further, the control unit 21, the scan control unit 24, the signal processing unit 28, the B-mode image data generating unit 30, and the DSC 32 are also constituted from a CPU and software. However, the signal processing unit 28, the B-mode image data generating unit 30, and the DSC 32 may be constituted from digital circuits or analog circuits. The above-mentioned software is stored in the storage unit 23. Further, the transmission delay patterns and reception delay patterns to be selected by the scan control unit 24 may be stored in the storage unit 23.

The DSC 32 converts (raster-converts) the B-mode image data generated by the B-mode image data generating unit 30 into ultrasonic image data that follows the normal scan system of television signals, and performs necessary image processing such as gradation processing to generate image data for display. Further, the DSC 32 generates synthesized data for color presentation of intima media in an ultrasonic image and superimposing of various information on the ultrasonic image based on the data outputted from the IMT measurement unit 31. Furthermore, an image processing part for performing image processing such as linear gradation processing including gain adjustment and contrast adjustment and nonlinear gradation processing including γ-correction may be provided at the downstream of the DSC 32.

The D/A converter 33 converts the image data for display converted in the DSC 32 into an analog signal and outputs the analog signal to the display unit 34.

The display unit 34 is a raster-scan type CRT display or LCD display, and displays moving images or still images of ultrasonic images, various setting screens, IMT measurement results, and so on based on the image signals analog-converted in the D/A converter 33. Although one display unit is provided in the embodiment, one or more other display unit may be provided for display of the various setting screens, for example.

Next, a function of the IMT measurement unit 31 in the ultrasonic diagnostic apparatus shown in FIG. 1 will be explained with reference to FIGS. 1 and 2.

Figure 2:
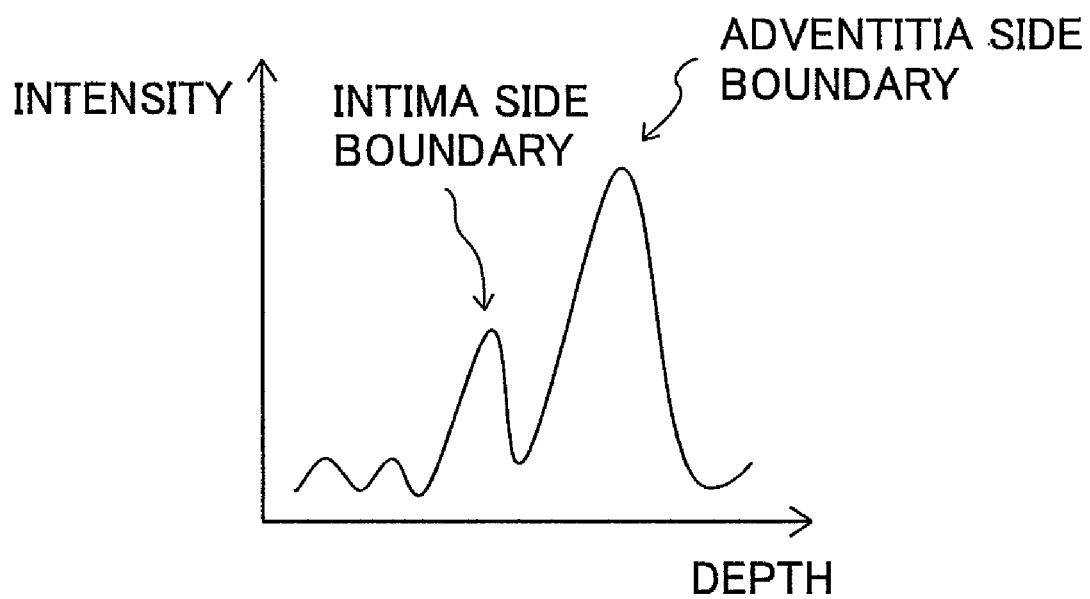
FIG. 2 is a schematic diagram showing intensity data representing a region including a section of a vessel wall.

FIG. 2 shows a change in a value of certain intensity data. Typically, in the case where a certain measurement line runs across a vessel wall in one position, peaks are observed in two positions at the boundary between the vascular lumen and the intima (hereinafter, also referred to as the intima side boundary) and the boundary between the media and the adventitia (hereinafter, also referred to as the adventitia side boundary) in the intensity data corresponding to the measurement line. Of them, the reflection of ultrasonic waves at the adventitia side boundary is stronger and the reflection at the intima side boundary is weaker, and therefore, the intensity of the peak has two levels. Accordingly, the intima side boundary and the adventitia side boundary are obtained by detecting such two peaks, and IMT is obtained by calculating a distance between the boundaries.

The envelope memory 40 stores envelope data supplied from the signal processing unit 28 in the live mode and stores envelope data supplied from the cine-memory 29 in the freeze mode.

The boundary detecting part 41 detects an intima side boundary and an adventitia side boundary based on the intensity data stored in the envelope memory 40. That is, the boundary detecting part 41 searches for a region where the intensity increases (a region where the intensity as shown in FIG. 2 rises) by difference calculation or differential calculation, and extracts, when the intensity difference between ends of the region is larger than a predetermined threshold value, the region as an intima side boundary or adventitia side boundary.

The ROI setting part 42 sets the region selected by the examiner within the B-mode image as a region of interest (ROI) for IMT measurement.

The search range setting part 43 sets a target region (search range) for boundary detection by the boundary detecting part 41. The search range setting part 43 sets the region of interest set by the ROI setting part 42 as the first search range, and then, resets the search range according to detection circumstances.

The threshold value setting part 44 sets a threshold value to be used by the boundary detecting part 41.

The error detecting part 45 determines whether or not a point of interest detected as a boundary is erroneously detected based on the relationship between the point of interest and the adjacent boundaries in the azimuth direction.

The IMT calculating part 46 calculates IMT values based on coordinate values (depths) of the detected intima side boundary and adventitia side boundary, and obtains the maximum value of IMT (maxIMT) from the IMT values, and further, calculates a mean value of IMT (meanIMT).

The IMT display processing part 47 generates image data for color presentation for displaying the detected boundaries in color on the ultrasonic image, position data for displaying the position of maxIMT by using an arrow or like, and measurement data representing measurement values of maxIMT and meanIMT, and outputs the data to the DSC 32.

In addition, a preprocessing part for performing image processing such as smoothing processing, contrast enhancement processing, edge enhancement processing, noise reducing processing on the intensity data stored in the envelope memory 40 may be further provided at the upstream of the boundary detecting part 41. In this case, it is efficient that the preprocessing is performed only on the region set as the ROI.

Next, a boundary detection operation and an IMT measurement operation to be performed in the ultrasonic diagnostic apparatus according to the embodiment will be explained with reference to FIGS. 1 and 3-5.

Ultrasonic imaging is started when the examiner brings the ultrasonic probe 100 (FIG. 1) in contact with the cervical part of a patient, and a B-mode image is displayed on the display unit 34.

Figure 3:
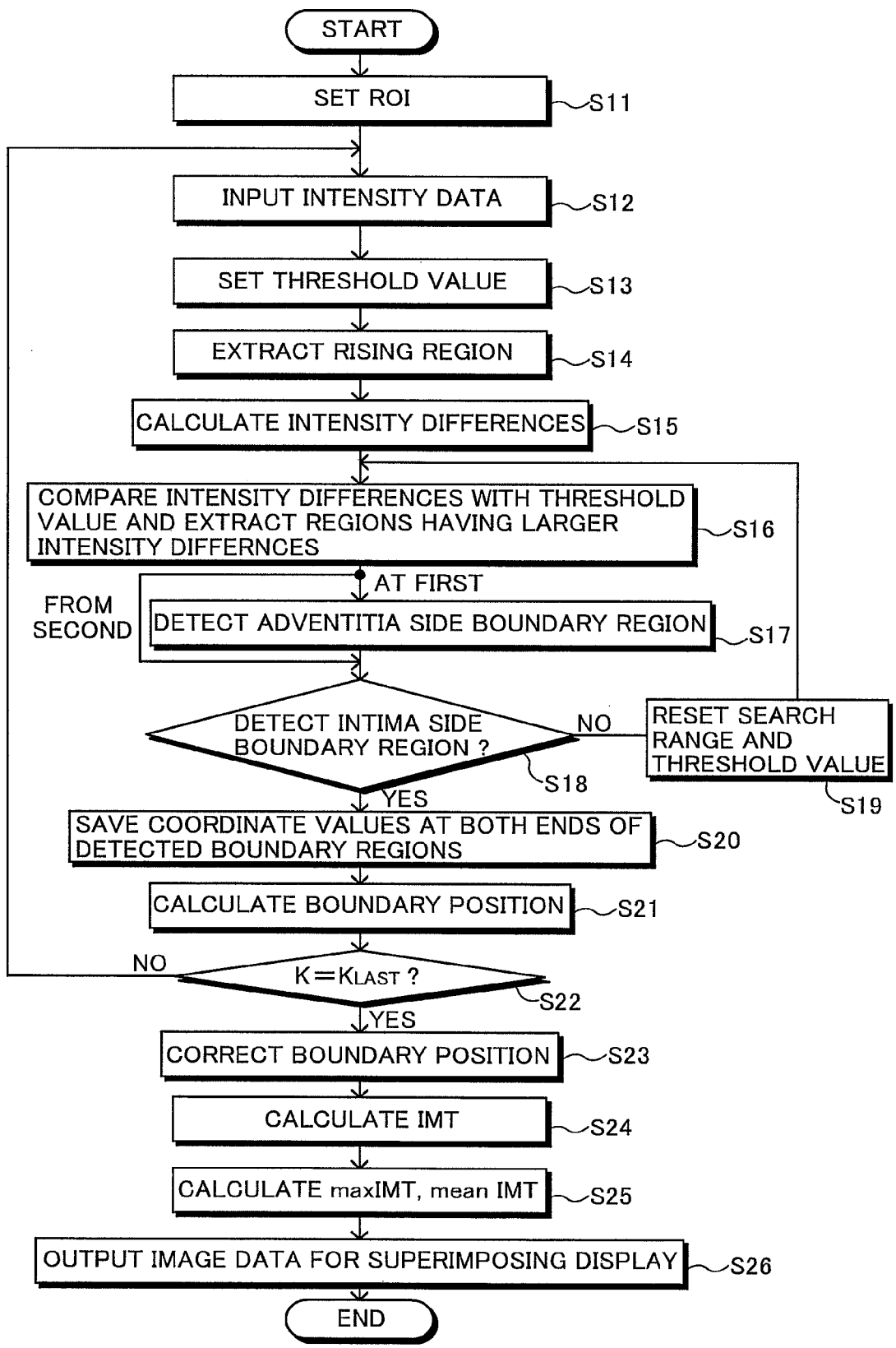
FIG. 3 is a flowchart showing a boundary detection operation and an IMT measurement operation in the ultrasonic diagnostic apparatus shown in FIG. 1.
Figure 4A:
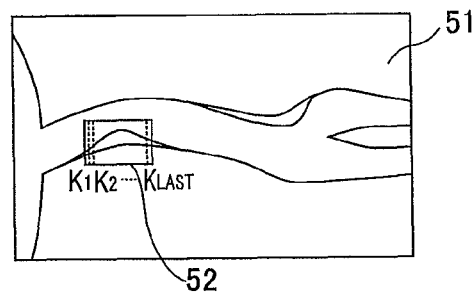
FIGS. 4A-4E are diagrams for explanation of the boundary detection operation.

At step S11 in FIG. 3, the examiner sets an ROI 52 for a portion of interest (e.g., a portion considered to be a plaque, the vicinity of the entrance of common carotid artery, vascular bifurcation, or the like) within a B-mode image 51 displayed on the screen as shown in FIG. 4A. In this regard, it is desirable to set the ROI 52 to include only one vessel wall section (i.e., not to include opposed two vessel walls). IMT measurement is performed with respect to each measurement line $K=K_1$ to $K_{LAST}$ within the ROI 52. The search range setting part 43 sets the length of the measurement line K as an initial set value of search range. In response, at step S12, intensity data corresponding to the search range is inputted to the boundary detecting part 41.

At step S13, the threshold value setting part 44 sets a threshold value to be used for boundary detection. As the threshold value, a value empirically obtained may be used or the threshold value used in the previous boundary detection may be used. When the threshold value is initially set, it is not necessary to reset the threshold value.

Figure 4B:
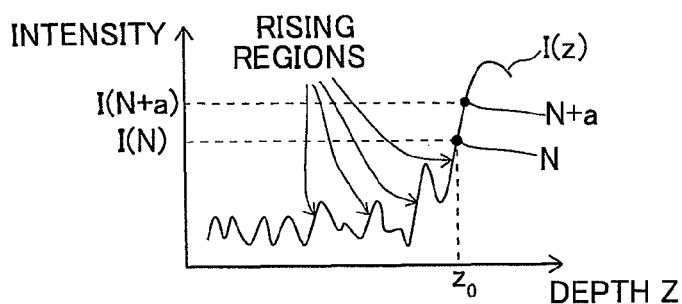

At step S14, as shown in FIG. 4B, the boundary detecting part 41 searches for and extract regions where the intensity rises (regions where the difference values or differential values are positive) in the intensity data included in the search range. For example, intensity value I(N) at a certain point of interest "N" and intensity value I(N+a) at the adjacent point "N+a" ($a \geq 1$) are compared and whether or not the difference value $\{I(N+a)-I(N)\}/\{(N+a)-(N)\}$ is positive is determined. Alternatively, differential value $dI(z)/dz$ ($z=z_0$) at a certain depth $z_0$ is calculated, and whether or not the differential value is positive is determined. The rising regions are candidate regions of intima side boundary or adventitia side boundary.

Figure 4C:
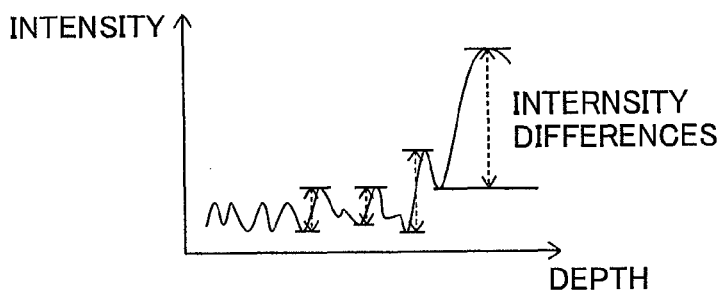

Then, at step S15, as shown in FIG. 4C, the boundary detecting part 41 calculates an amount of change in intensity (an intensity difference) between both ends of the rising region of intensity.

At step S16, the boundary detecting part 41 compares the intensity difference in the rising region with a threshold value, and extracts two regions having the intensity differences larger than the threshold value as an intima side boundary and an adventitia side boundary. In this regard, the region having the larger intensity difference is considered to be an adventitia side boundary region (step S17), and the region having the smaller intensity difference is considered to be an intima side boundary region (step S18). Further, if only one region having the intensity difference larger than the threshold value is detected, the region is considered to be an adventitia side boundary region.

Figure 4D:
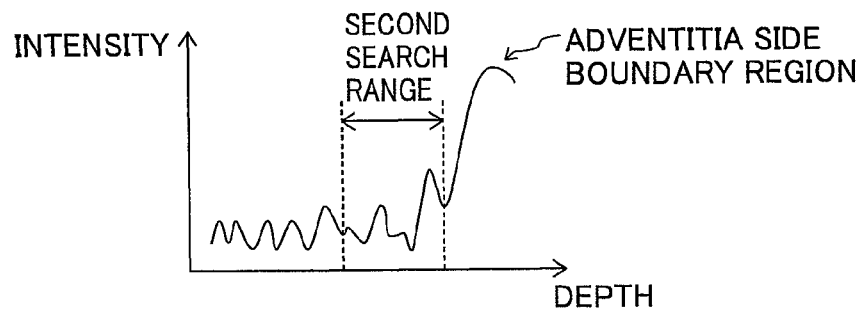

If no intima side boundary region is detected at step S18, the search range setting part 43 sets a new search range and the threshold value setting part 44 sets a new threshold value at step S19. As the search range, as shown in FIG. 4D, a predetermined range from the adventitia side boundary region detected at step S17 is set. For example, the next search range may be determined with reference to clinically possible IMT values, or may be numerically determined to be within 50% of the previous search range. On the other hand, as the threshold value, a value lower than the threshold value used at step S16 is set (e.g., 80% of the previous threshold value).

Thereby, at step S16, searching for the intima side boundary region is performed under the reset conditions (the search range and the threshold value). The searching step 16 and the search condition setting steps S18-S19 are performed until the intima side boundary region is detected while the search range is gradually narrowed and the threshold value is gradually decreased.

Figure 4E:
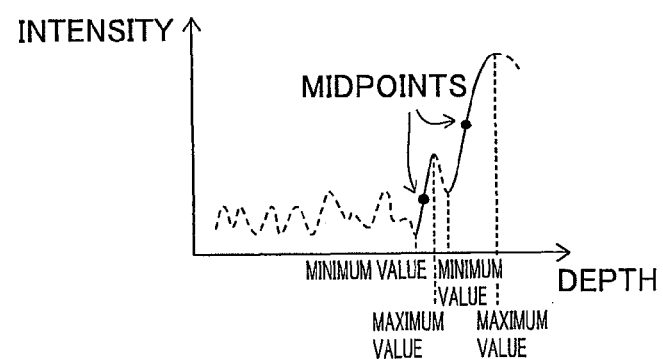

Then, at step S20, as shown in FIG. 4E, the boundary detecting part 41 saves coordinate values at both ends of the detected each boundary region (i.e., the maximum value and the minimum value of the depth).

At step S21, the boundary detecting part 41 determines positions (coordinates) of the intima side boundary and the adventitia side boundary based on the saved maximum values and minimum values. The boundary position may be the maximum value or the minimum value in each boundary region, or may be a midpoint between the maximum value and the minimum value. The data representing the boundary positions (boundary data) is outputted to the error detecting part 45 and temporarily stored for determination whether or not there is a detection error.

Such boundary detection processing (steps S12-S21) is repeated until the measurement line $K=K_1, K_2, \ldots$ within the ROI 52 reaches the right end ($K=K_{LAST}$) as shown in FIG. 4A (step S22).

Then, at step S23, the error detecting part 45 determines whether or not there is a detection error with respect to the boundaries obtained at step S21, and, if there is a detection error, performs correction (detection of true boundary). The corrected boundary data is outputted to the IMT calculating part 46. The correction operation will be specifically explained later.

Figure 5:
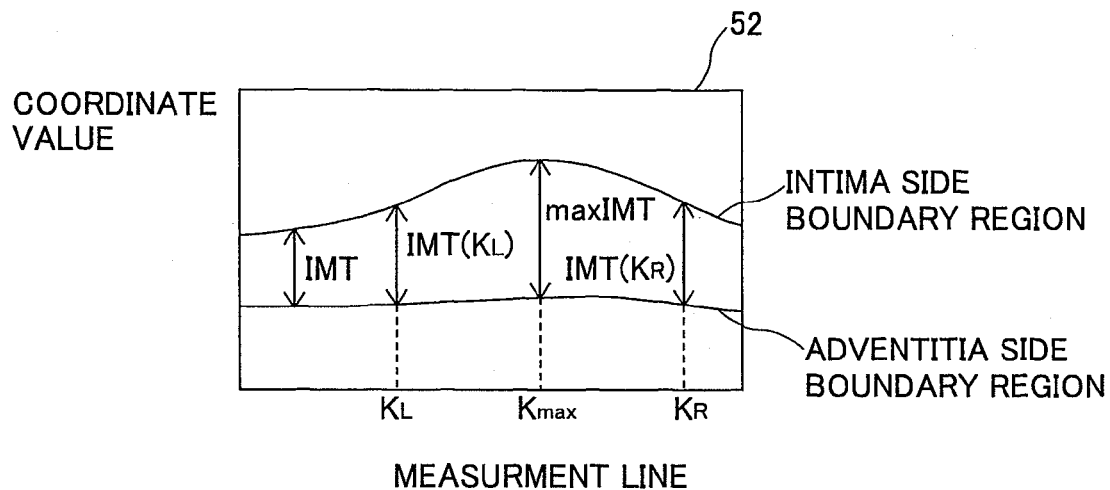
FIG. 5 is a diagram for explanation of the IMT measurement operation.

At step S24, as shown in FIG. 5, the IMT calculating part 46 calculates IMT for each of measurement lines $K_1, K_2, \ldots$ by obtaining a coordinate value difference between the intima side boundary and the adventitia side boundary.

At step S25, the IMT calculating part 46 obtains the maximum value of IMT (maxIMT) among the IMTs calculated for the respective measurement lines, and acquires the measurement line $K_{max}$ from which the maxIMT is obtained. Further, the IMT calculating part 46 acquires IMT ($K_L$) and IMT ($K_R$) in the measurement lines $K_L$ and $K_R$ at a predetermined distance (e.g., 1 cm apart at both sides) from the $K_{max}$, and calculates a mean value meanIMT=$\{$maxIMT+IMT($K_L$)+IMT($K_R$)$\}/3$ of them.

Figure 6:
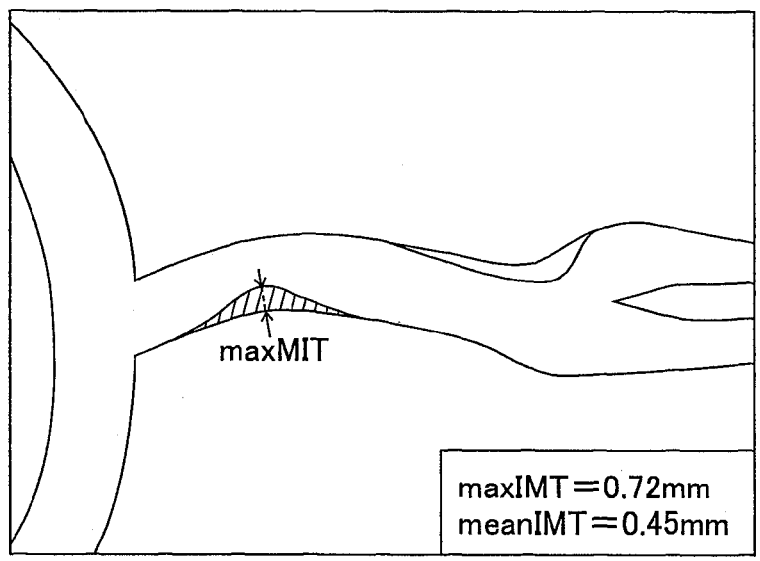
FIG. 6 shows an image in which intima media is displayed in superposition on a B-mode image.

At step S26, the IMT display processing part 47 generates image data for displaying the boundaries in color based on the boundary data outputted from the boundary detecting part 41 and outputs the image data to the DSC 32. Further, the display processing part 47 outputs position data for showing the position where the maxIMT is obtained by using an arrow or like, and measurement data representing measurement values such as maxIMT. Thereby, as shown in FIG. 6, the intima media or the boundary thereof is displayed in color and the position of the maxIMT and the values of the maxIMT and the meanIMT are displayed on the B-mode image generated in the B-mode image data generating unit 30.

Next, the correction operation at step S23 in FIG. 3 will be explained with reference to FIGS. 1, 7, 8A and 8B.

Figure 7:
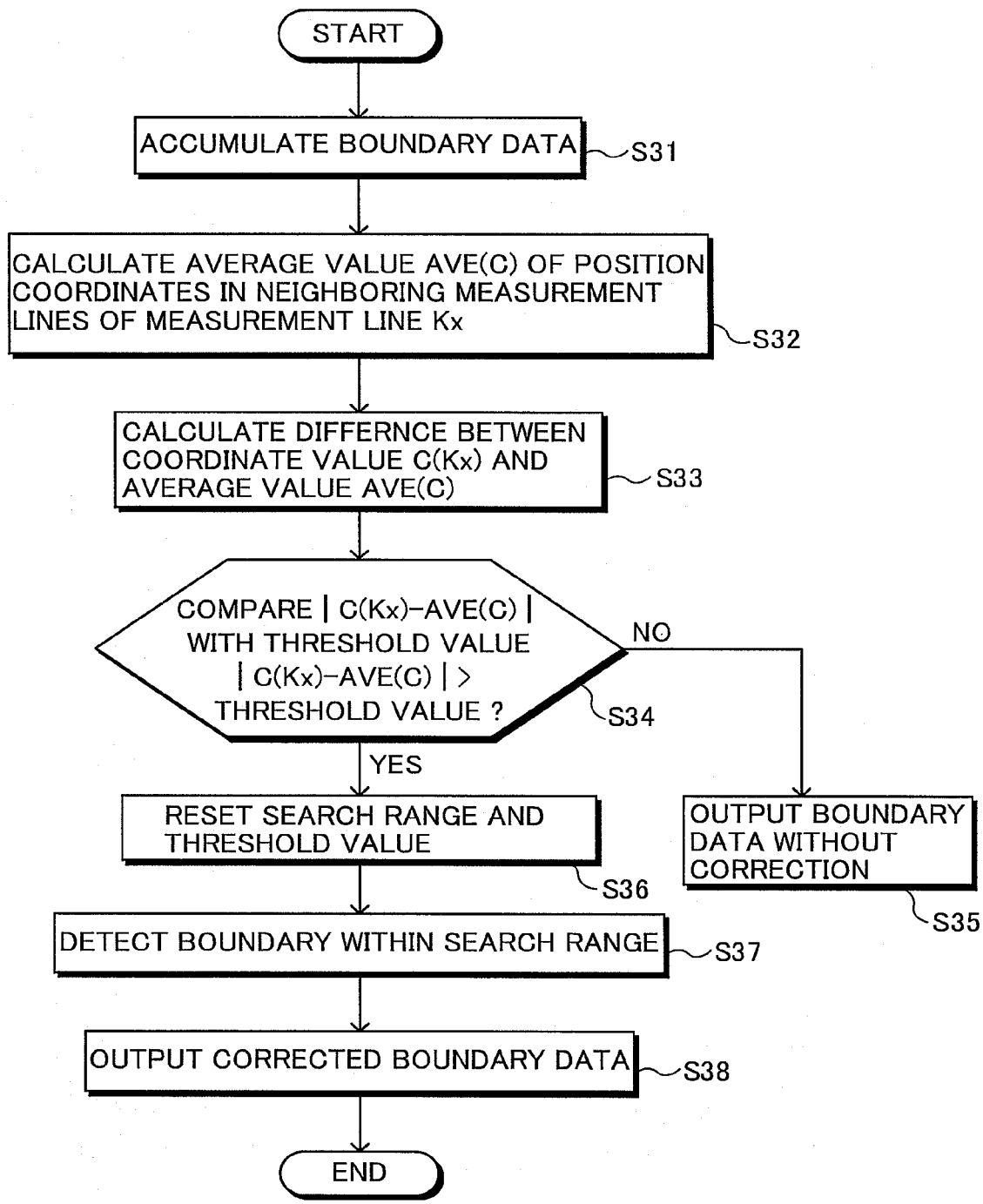
FIG. 7 is a flowchart showing a correction operation in the ultrasonic diagnostic apparatus shown in FIG. 1.

At step S31 in FIG. 7, the error detecting part 45 shown in FIG. 1 accumulates boundary data detected with respect to each measurement line by the boundary detecting part 41 for one frame.

Figure 8A:
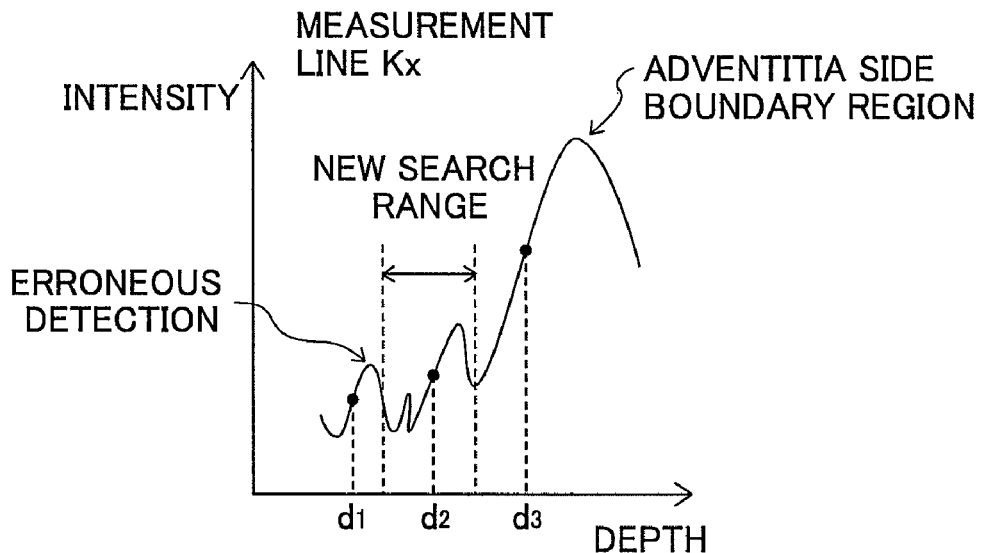
FIGS. 8A and 8B are diagrams for explanation of the correction operation.
Figure 8B:
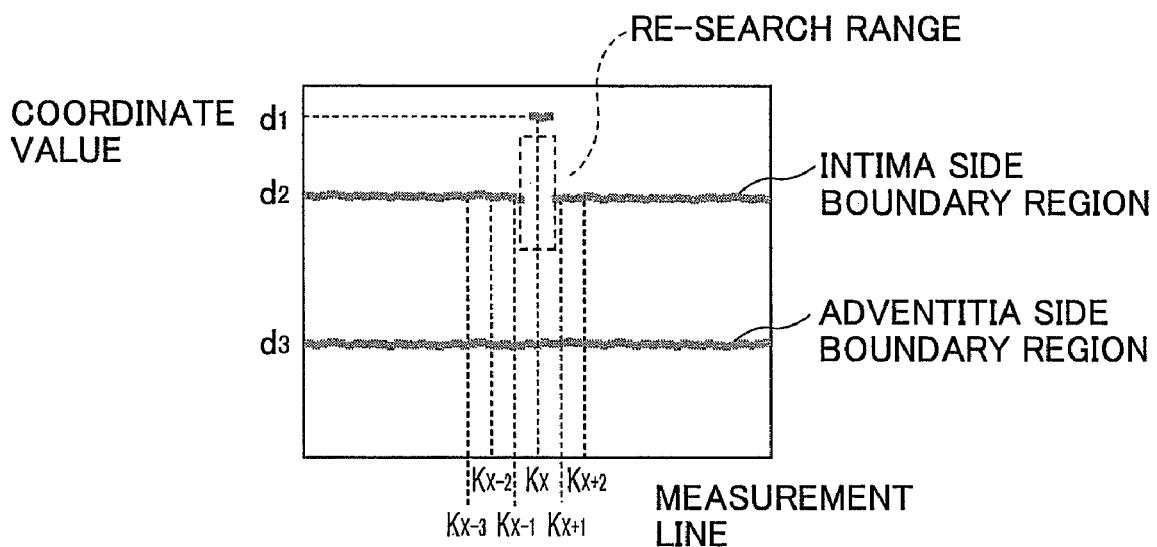
Figure 9:
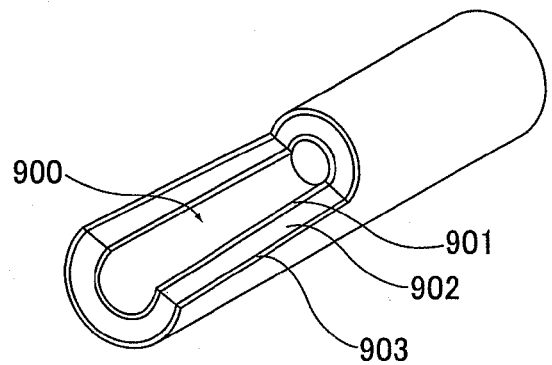
FIG. 9 is a diagram for explanation of an artery structure.
Figure 10:
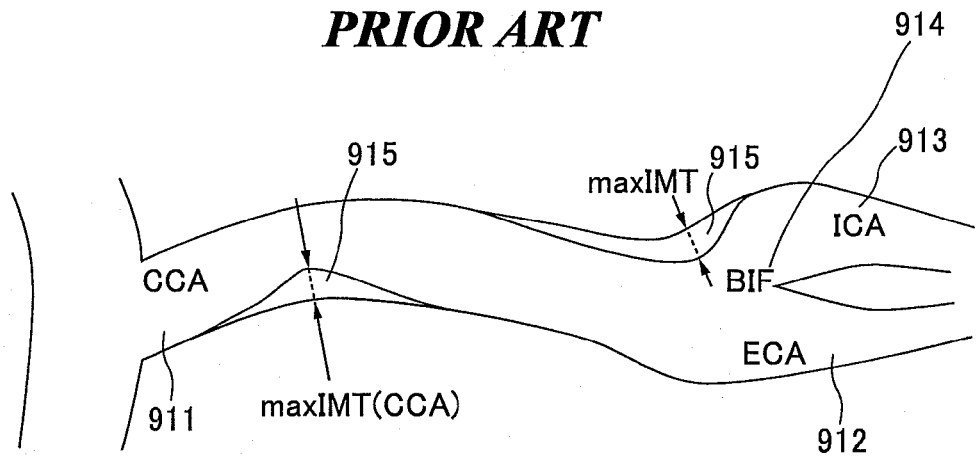
FIG. 10 shows a carotid artery shape and a measurement position of maxIMT.
Figure 11:
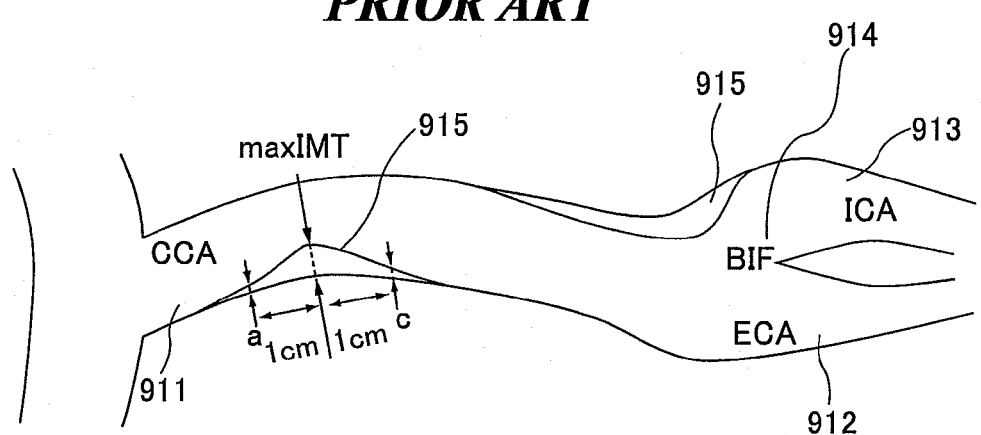
FIG. 11 shows mean carotid artery shape and a measurement position of meanIMT.
Figure 12:
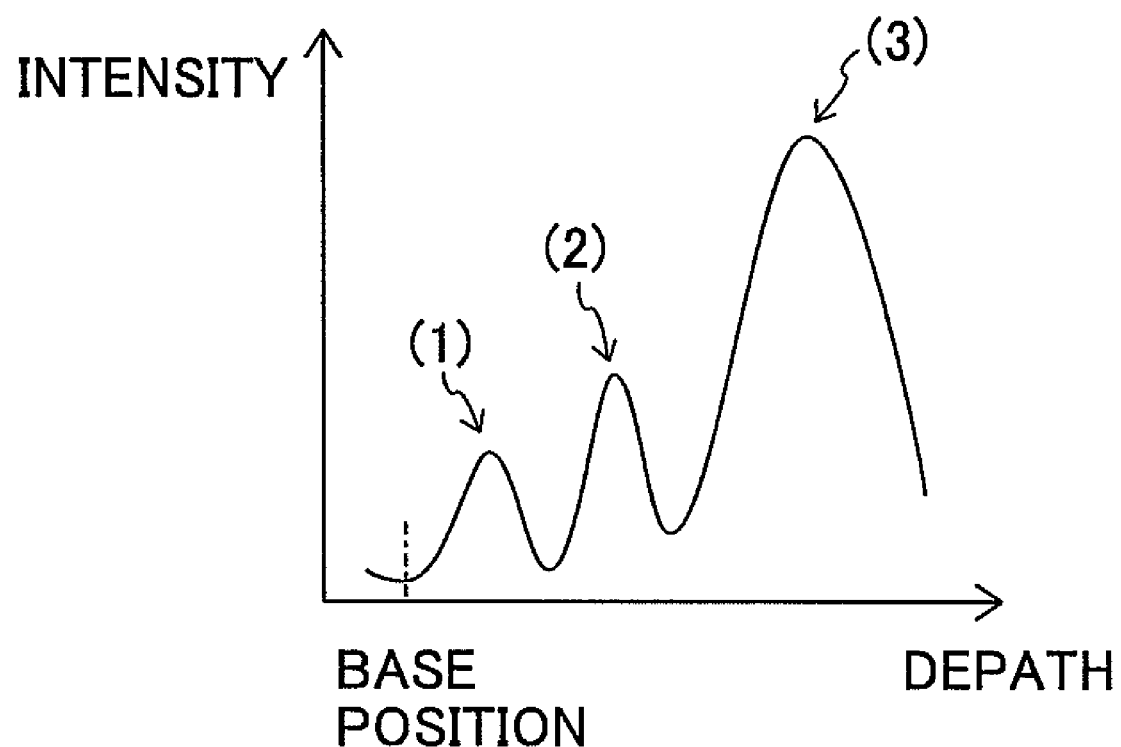
FIG. 12 is a diagram for explanation of a boundary detection error.

Here, in the case where a peak due to noise is erroneously detected as an intima side boundary in a certain measurement line $K_x$ as shown in FIG. 8A, the continuity of the intima side boundary is lost as shown in FIG. 8B. The error detecting part 45 determines whether or not there is a boundary detection error by focusing attention on the continuity in the azimuth direction (a direction perpendicular to the depth direction).

That is, at step S32, as shown in FIG. 8B, with respect to the coordinate value C ($K_x$) detected in the measurement line $K_x$ of interest, an average value AVE (C) of boundary coordinate values C($K_{x-1}$), C($K_{x-2}$), ... detected in the neighboring measurement lines $K_{x-1}, K_{x-2}, \ldots$ or $K_{x+1}, K_{x+2}, \ldots$ (prior or subsequent, or both prior and subsequent thereto) is calculated. Then, at step S33, the difference between the coordinate value C($K_x$) and the AVE(C) is calculated.

At step S34, the error detecting part 45 determines whether or not there is a detection error by comparing the difference between the coordinate value C ($K_x$) and the AVE (C) with a predetermined threshold value. As the threshold value, for example, a fixed value that is clinically acceptable may be used, or the difference between the maximum value and the minimum value of boundary coordinates in the nearby frame may be used.

As a result of determination at step S34, in the case where the difference between the coordinate value C($K_x$) and the AVE (C) is smaller than the threshold value, it is considered that there is no boundary detection error, and the boundary data is outputted to the IMT calculating part 46 without correction (step S35).

On the other hand, in the case where the difference between the coordinate value C ($K_x$) and the AVE (C) is equal to or larger than the threshold value, the boundary of the coordinate value C($K_x$) is determined to have been erroneously detected, and the search is made again for detection of true boundary. At step S36, the search range setting part 43 resets a search range based on (i) positions of neighboring boundaries in the azimuth direction of the boundary that has been erroneously detected or (ii) a position of another boundary existing in the depth direction of the boundary that has been erroneously detected. For example, in the case where the boundary that has been erroneously detected is located in a position shallower (or deeper) than the boundaries in the neighboring measurement lines, the region deeper (or shallower) than the boundary that has been erroneously detected is set as a new search range as shown in FIGS. 8A and 8B. Alternatively, a new search range maybe set with reference to the position of the adventitia side boundary on the measurement line $K_x$ in which there has been a detection error (e.g., in a range of several millimeters to the shallower side from the adventitia side boundary). As the threshold value, a value used in the previous boundary detection may be used, or a smaller value (e.g., 80%) may be set and used.

Then, at step S37, processing for detecting the true boundary is performed with respect to the boundary data corresponding to the new search range. The boundary detection processing is the same as that at steps S16-S21 shown in FIG. 2.

At step S38, the error detecting part 45 outputs the corrected boundary data to the IMT calculating part 46.

As described above, according to the embodiment, boundaries can be easily and correctly detected by focusing attention on the gradient of intensity data values and amounts of change in intensity. Especially, by gradually decreasing the search range and the threshold value, the intima side boundary having relatively small intensity can be detected separately from the noise. Further, according to the embodiment, whether or not there is a detection error is determined based on the position relationship among boundaries in the azimuth direction, and thus, rational determination results can be obtained. Furthermore, according to the embodiment, in the case where there is a detection error, the search range is reset based on the position relationship among the neighboring boundaries and the position of the adventitia side boundary and the true boundary is searched for again, and thus, correction with high accuracy can be performed. Consequently, nearly error-free maxIMT can be obtained and highly reliable medical diagnoses can be performed.

In the above explanation, although boundaries are detected based on the intensity data, even data that does not directly represent intensity may be utilized as long as the data corresponds to the intensity of reflection of ultrasonic waves in the object. For example, envelope data on which various kinds of signal processing have been performed may be used according to need.

The invention claimed is:

1. An ultrasonic diagnostic apparatus comprising:
   an ultrasonic probe for transmitting ultrasonic waves to an object to be inspected and receiving ultrasonic echoes generated by reflection of the ultrasonic waves in the object to output reception signals;
   signal processing means for performing at least envelope detection processing on the reception signals outputted from said ultrasonic probe to generate envelope data;
   boundary detecting means for detecting two boundaries representing intima media of a blood vessel; and
   IMT (intima media thickness) calculating means for calculating an IMT of the blood vessel based on the two boundaries detected by said boundary detecting means;
   wherein said boundary detecting means searches for rising regions, where a value of the envelope data increases along a measurement line, based on one of difference calculation and differential calculation of the envelope data, calculates amounts of change in the value of the envelope data between both ends of the rising regions, and compares the amounts of change in the value of the envelope data with a threshold value to detect the two boundaries.

2. The ultrasonic diagnostic apparatus according to claim 1, further comprising:
   threshold value setting means for setting the threshold value to be compared with the amounts of change in the value of the envelope data;
   wherein said boundary detecting means detects as a boundary a rising region in which an amount of change in the value of the envelope data is larger than the threshold value set by said threshold value setting means.

3. The ultrasonic diagnostic apparatus according to claim 2, wherein said threshold value setting means resets the threshold value to a smaller value in a case where at least one of the two boundaries is not detected.

4. The ultrasonic diagnostic apparatus according to claim 1, further comprising:
   search range setting means for setting a search range for searching for the two boundaries;
   wherein said boundary detecting means searches for the two boundaries based on the envelope data within the search range set by said search range setting means.

5. The ultrasonic diagnostic apparatus according to claim 4, wherein said search range setting means resets, when only one boundary is detected by said boundary detecting means, a search range for searching for the other boundary based on a position of the one boundary.

6. The ultrasonic diagnostic apparatus according to claim 4, further comprising:
   error detecting means for detecting a detection error of a boundary in said boundary detecting means based on a position relationship among boundaries in an azimuth direction;
   wherein said search range setting means resets, when a detection error of a boundary is detected by said error detecting means, a search range based on one of (i) positions of neighboring boundaries in the azimuth direction of the boundary that has been erroneously detected and (ii) a position of another boundary existing in a depth direction of the boundary that has been erroneously detected; and
   said boundary detecting means searches for a boundary within the reset search range.

7. The ultrasonic diagnostic apparatus according to claim 1, further comprising:
   error detecting means for detecting a detection error of a boundary in said boundary detecting means based on a position relationship among boundaries in an azimuth direction.

8. The ultrasonic diagnostic apparatus according to claim 7, wherein said error detecting means determines whether or not there is a detection error of a boundary based on a difference between a coordinate value of the boundary and an average value of coordinate values of neighboring boundaries in the azimuth direction of the boundary.

9. The ultrasonic diagnostic apparatus according to claim 1, wherein said IMT calculating means obtains a maximum value of the IMT and a position where the IMT is largest based on IMTs calculated in plural measurement lines, respectively.

10. An IMT (intima media thickness) measurement method of measuring an IMT of a blood vessel based on envelope data in an ultrasonic diagnostic apparatus for transmitting ultrasonic waves to an object to be inspected and receiving ultrasonic echoes generated by reflection of the ultrasonic waves in the object to obtain reception signals, and performing at least envelope detection processing on the reception signals to generate the envelope data, said method comprising the steps of:
   (a) detecting two boundaries representing intima media of the blood vessel; and
   (b) calculating the IMT of the blood vessel based on the two boundaries detected at step (a);
   wherein step (a) includes searching for rising regions, where a value of the envelope data increases along a measurement line, based on one of difference calculation and differential calculation of the envelope data, calculating amounts of change in the value of the envelope data between both ends of the rising regions, and comparing the amounts of change in the value of the envelope data with a threshold value to detect the two boundaries.

11. The IMT measurement method according to claim 10, further comprising the step of:
   (c) setting the threshold value to be compared with the amounts of change in the value of the envelope data;
   wherein step (a) includes detecting as a boundary a rising region in which an amount of change in the value of the envelope data is larger than the threshold value set at step (c).

12. The IMT measurement method according to claim 10, further comprising the step of:
   (d) setting a search range for searching for the two boundaries;
   wherein step (a) includes searching for the two boundaries based on the envelope data within the search range set at step (d).

13. The IMT measurement method according to claim 12, further comprising the step of:
   (e) detecting a detection error of a boundary at step (a) based on a position relationship among boundaries in an azimuth direction;
   wherein step (d) includes resetting, when a detection error of a boundary is detected at step (e), a search range based on one of (i) positions of neighboring boundaries in the azimuth direction of the boundary that has been erroneously detected and (ii) a position of another boundary existing in a depth direction of the boundary that has been erroneously detected; and
   step (a) includes searching for a boundary within the reset search range.

14. The IMT measurement method according to claim 10, further comprising the step of:
   (e) detecting a detection error of a boundary at step (a) based on a position relationship among boundaries in an azimuth direction.

15. The IMT measurement method according to claim 10, wherein step (b) includes obtaining a maximum value of the IMT and a position where the IMT is largest based on IMTs calculated in plural measurement lines, respectively.

16. An IMT (intima media thickness) measurement program embodied in non-transitory form on a computer readable medium, for measuring an IMT of a blood vessel based on envelope data in an ultrasonic diagnostic apparatus for transmitting ultrasonic waves to an object to be inspected and receiving ultrasonic echoes generated by reflection of the ultrasonic waves in the object to obtain reception signals, and performing at least envelope detection processing on the reception signals to generate the envelope data, said program activating a CPU to execute the procedures of:
   (a) detecting two boundaries representing intima media of the blood vessel; and
   (b) calculating the IMT of the blood vessel based on the two boundaries detected at procedure (a);
   wherein procedure (a) includes searching for rising regions, where a value of the envelope data increases along a measurement line, based on one of difference calculation and differential calculation of the envelope data, calculating amounts of change in the value of the envelope data between both ends of the rising regions, and comparing the amounts of change in the value of the envelope data with a threshold value to detect the two boundaries.

17. The IMT measurement program according to claim 16, further activating the CPU to execute the procedure of:
   (d) setting a search range for searching for the two boundaries;
   wherein procedure (a) includes searching for the two boundaries based on the envelope data within the search range set at procedure (d).

18. The IMT measurement program according to claim 17, further activating the CPU to execute the procedure of:
   (e) detecting a detection error of a boundary at procedure (a) based on a position relationship among boundaries in an azimuth direction;
   wherein procedure (d) includes resetting, when a detection error of a boundary is detected at procedure (e), a search range based on one of (i) positions of neighboring boundaries in the azimuth direction of the boundary that has been erroneously detected and (ii) a position of another boundary existing in a depth direction of the boundary that has been erroneously detected; and
   procedure (a) includes searching for a boundary within the reset search range.

19. The IMT measurement program according to claim 16, further activating the CPU to execute the procedure of:
   (e) detecting a detection error of a boundary at procedure (a) based on a position relationship among boundaries in an azimuth direction.

20. The IMT measurement program according to claim 16, wherein procedure (b) includes obtaining a maximum value of the IMT and a position where the IMT is largest based on IMTs calculated in plural measurement lines, respectively.

* * * * *